(12) United States Patent
Dowdy et al.

(10) Patent No.: US 6,295,082 B1
(45) Date of Patent: *Sep. 25, 2001

(54) CAMERA HEAD WITH DIGITAL MEMORY FOR STORING INFORMATION ABOUT THE IMAGE SENSOR

(75) Inventors: Clifford A. Dowdy, Piedmont; William P. Fields; Garry L. Womack, both of Edmond; Michael R. Burnett, Oklahoma City, all of OK (US)

(73) Assignee: Smith & Nephew, Inc., Memphis, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/659,427

(22) Filed: Jun. 6, 1996

Related U.S. Application Data

(63) Continuation of application No. 08/200,197, filed on Feb. 23, 1994, now abandoned.

(51) Int. Cl.[7] .................................................. H04N 7/18
(52) U.S. Cl. ............................................. 348/72; 348/232
(58) Field of Search ................................. 348/72, 74, 75, 348/65, 231, 232, 233, 247; H04N 7/18

(56) References Cited

U.S. PATENT DOCUMENTS

| | | | |
|---|---|---|---|
| 4,509,128 | * | 4/1985 | Coppola et al. ................... 364/483 |
| 4,539,586 | * | 9/1985 | Danna et al. ........................ 128/6 |
| 4,601,284 | | 7/1986 | Arakawa et al. . |
| 4,667,230 | | 5/1987 | Arakawa et al. . |
| 4,731,864 | * | 3/1988 | Modla ................................ 348/231 |
| 4,746,975 | * | 5/1988 | Ogiu .................................... 128/4 |
| 4,845,555 | * | 7/1989 | Yabe et al. ............................ 128/4 |
| 4,860,094 | * | 8/1989 | Hibino et al. .......................... 128/6 |
| 4,870,488 | * | 9/1989 | Ikuno ..................................... 128/6 |
| 4,893,185 | * | 1/1990 | Fukushima et al. ............. 358/213.17 |
| 4,951,135 | * | 8/1990 | Sasagawa et al. .................... 348/69 |
| 4,980,763 | | 12/1990 | Lia ...................................... 358/98 |
| 4,996,975 | * | 3/1991 | Nakamura .............................. 128/6 |
| 5,040,054 | * | 8/1991 | Schmidt et al. ...................... 348/232 |
| 5,070,401 | * | 12/1991 | Salvati et al. ....................... 364/560 |
| 5,089,979 | * | 2/1992 | McEachern et al. ............. 364/571.04 |
| 5,255,188 | * | 10/1993 | Telepko .............................. 364/413.27 |
| 5,315,383 | * | 5/1994 | Yabe et al. ........................... 348/68 |
| 5,400,267 | * | 3/1995 | Denen et al. ......................... 364/552 |

FOREIGN PATENT DOCUMENTS

| | | |
|---|---|---|
| 0 534 198 A2 | 9/1992 | (EP) . |
| 0534198 | 3/1993 | (EP) . |
| 3183273 | 8/1991 | (JP) . |
| WO 91/10320 | 7/1991 | (WO) . |

OTHER PUBLICATIONS

Gilbert F. Amelio, "Charge–Coupled Devices", Scientific American, Feb. 1974, vol. 230, No. 2, pp. 22–31.

* cited by examiner

Primary Examiner—Richard Lee
(74) Attorney, Agent, or Firm—Fish & Richardson P.C.

(57) ABSTRACT

An apparatus sends electrical signals that represent an optical image to a processor for conversion to video signals suitable for display on a display device. The apparatus includes a device for insertion into a region to be viewed for developing an optical image of the region, an imager for generating electrical signals that represent the optical image, and a digital memory for storing information about the imager. The device is adapted to be connected to the processor so that the processor can receive the electrical signals from the imager and obtain information from the digital memory. The processor uses the information from the digital memory in performing the conversion.

40 Claims, 4 Drawing Sheets

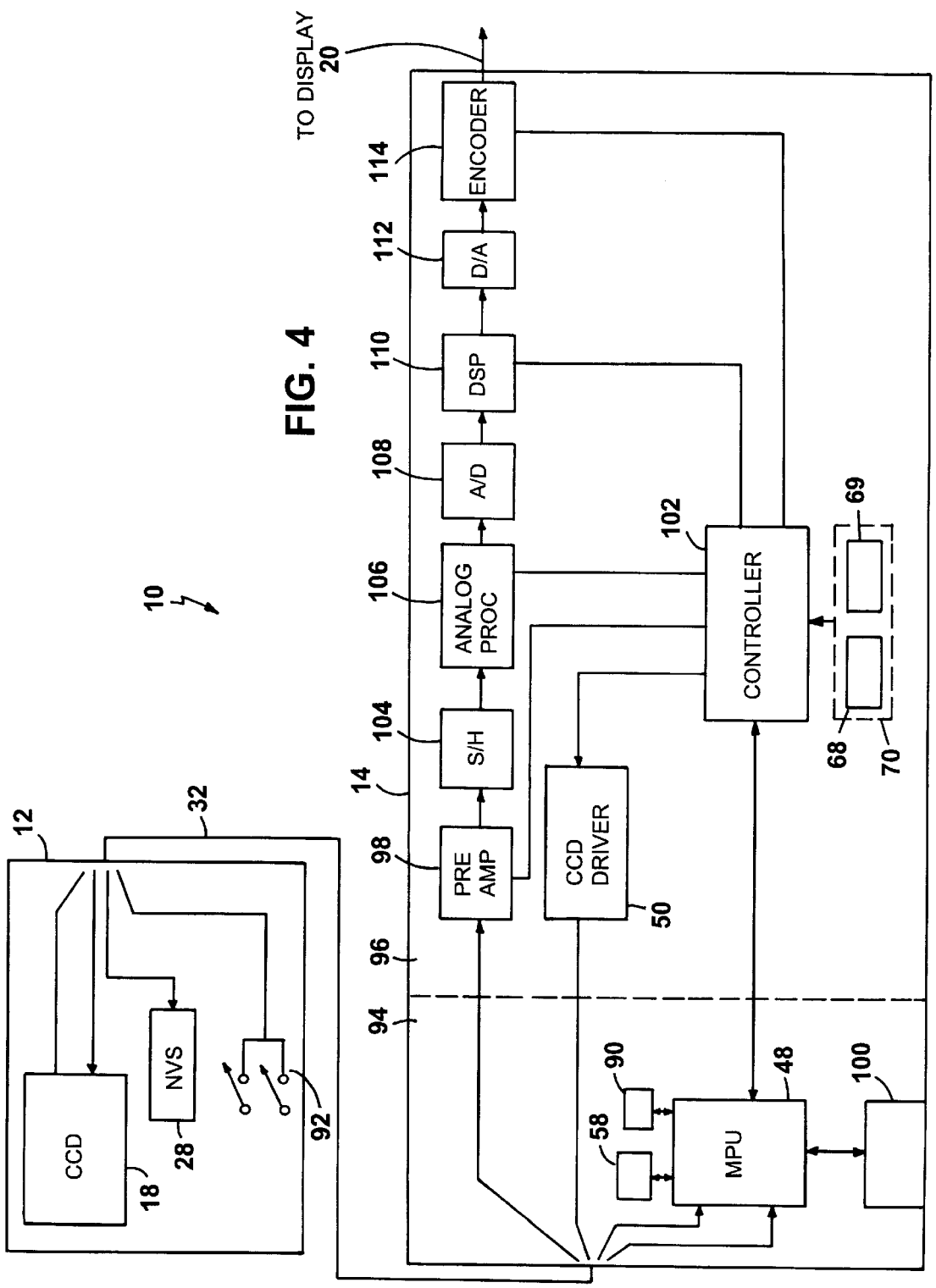

CAMERA HEAD WITH DIGITAL MEMORY FOR STORING INFORMATION ABOUT THE IMAGE SENSOR

This is a continuation of application Ser. No. 08/200,197, filed Feb. 23, 1994, now abandoned.

BACKGROUND OF THE INVENTION

The invention relates to camera heads for use with remote video display systems such as video endoscopy systems, borescopes, and other devices.

Remote video display systems display a view of the interior of a body cavity or another visually inaccessible, remote location on a video monitor. Generally, a remote video display system includes a camera processor and a camera head having an endoscope for insertion into the remote location. The camera head produces electrical signals representing an image of the remote location, and the camera processor processes the electrical signals for display on the video monitor. To produce the electrical signals, a solid state imaging device such as a charge coupled device ("CCD") is located in the tip of the endoscope or in the camera head.

The camera head and endoscope are typically detachable as a unit from the control unit so that a variety of camera heads can be used with a single control unit. This offers a number of advantages. For example, if a first camera head fails, the control unit can be operated with another camera head while the first camera head is being serviced. Also, different types of camera heads, each of which may be most useful for certain procedures, can be used with a single control unit so as to avoid the expense of purchasing and maintaining multiple control units.

SUMMARY OF THE INVENTION

In one general aspect, this invention features an apparatus for providing electrical signals that represent an optical image to a processor for conversion to video signals suitable for display on a display device. The apparatus includes a device for insertion into a region to be viewed for developing an optical image of the region, an imager for generating electrical signals that represent the optical image, and a digital memory for storing information about the imager. The device is adapted to be connected to the processor so that the processor can receive the electrical signals from the imager and obtain information from the digital memory. The processor uses the information from the digital memory in performing the conversion.

Preferred embodiments of the invention include one or more of the features described below.

The digital memory stores information about the configuration of the imager. This information can include the location of the imager relative to the device. For example, the information identifies whether the imager is located at the distal end or the proximal end of the device. The imager is a charge coupled device. The information identifies an optical format size of the charge coupled device.

The digital memory also stores information about variations in performance characteristics of the imager relative to nominal performance characteristics. When the apparatus includes optics, the information in the digital memory accounts for variations in performance characteristics of the optics relative to nominal performance characteristics. Similarly, when the imager includes a charge coupled device or a cable for connection to the processor, the information accounts for variations in performance characteristics of the charge coupled device or the cable relative to nominal performance characteristics. The information also identifies variations in luminance and color reproduction by the imager.

When the apparatus is designed for application to particular regions, the information identifies characteristics of the region to be viewed by the imager. This allows the processor to optimize the conversion for parameters that are desirable in a particular application.

The digital memory is updated by the processor. For example, the digital memory stores run time information that measures wear on the imager, and the processor updates the run time information from time to time.

In one embodiment, the digital memory is a non-volatile storage device, and can be implemented using an EEPROM.

In another aspect, the invention features an apparatus for representing an optical image as video signals suitable for display on a display device. The apparatus includes a device for producing electrical signals representative of an optical image of a region to be viewed, and having a portion for insertion into the region to be viewed for developing an optical image of the region, an imager for generating electrical signals that represent the optical image, and a digital memory for storing information about the device. The apparatus also includes a processor that receives the electrical signals from the imager and converts the electrical signals into video signals. The processor also obtains information from the digital memory and uses the information in the conversion.

Preferred embodiments include one or more of the features described below.

When the information stored in the digital memory identifies the configuration of the device, the processor modifies the conversion based on the configuration. This allows the processor to automatically optimize the conversion for different configurations of the device.

The processor also stores nominal values of performance characteristics for the device. In this case, the digital memory identifies variations in performance characteristics of the device relative to the nominal performance characteristics, and the processor modifies the conversion based on the variations in performance characteristics. This allows the processor to further optimize the conversion to account for characteristics of the particular device to which it is attached.

When the processor updates information, such as run time information, in the digital memory, the processor only does so at times at which it is not converting the electrical signals into video signals. Typically, the processor converts the electrical signals into video signals during a first time period and ignores the electrical signals during a second time period. Thus, to avoid interference of the information being updated with the electrical signals, the processor updates the information stored in the digital memory only during the second time period.

The apparatus also includes a driver that produces driving signals that drive the imager. In this case, when the digital memory identifies a configuration of the device, the processor signals the driver to modify the driving signals based on the configuration of the device.

The digital memory also stores verification information that verifies whether the information stored in the digital memory is valid. The processor uses the verification information to determine whether the information stored in the digital memory is valid and whether the processor has received the information correctly.

Some embodiments also include a memory having entries in which are stored signal processing parameters used by the processor in performing the conversion. In this case, the processor modifies the conversion by modifying entries of the memory that relate to information received from the digital memory.

Other features and advantages of the invention will become apparent from the following detailed description, and from the claims.

BRIEF DESCRIPTION OF THE DRAWING

FIG. 4 is a block diagram of a video endoscopy system.

DESCRIPTION OF PREFERRED EMBODIMENTS

Figure 1:
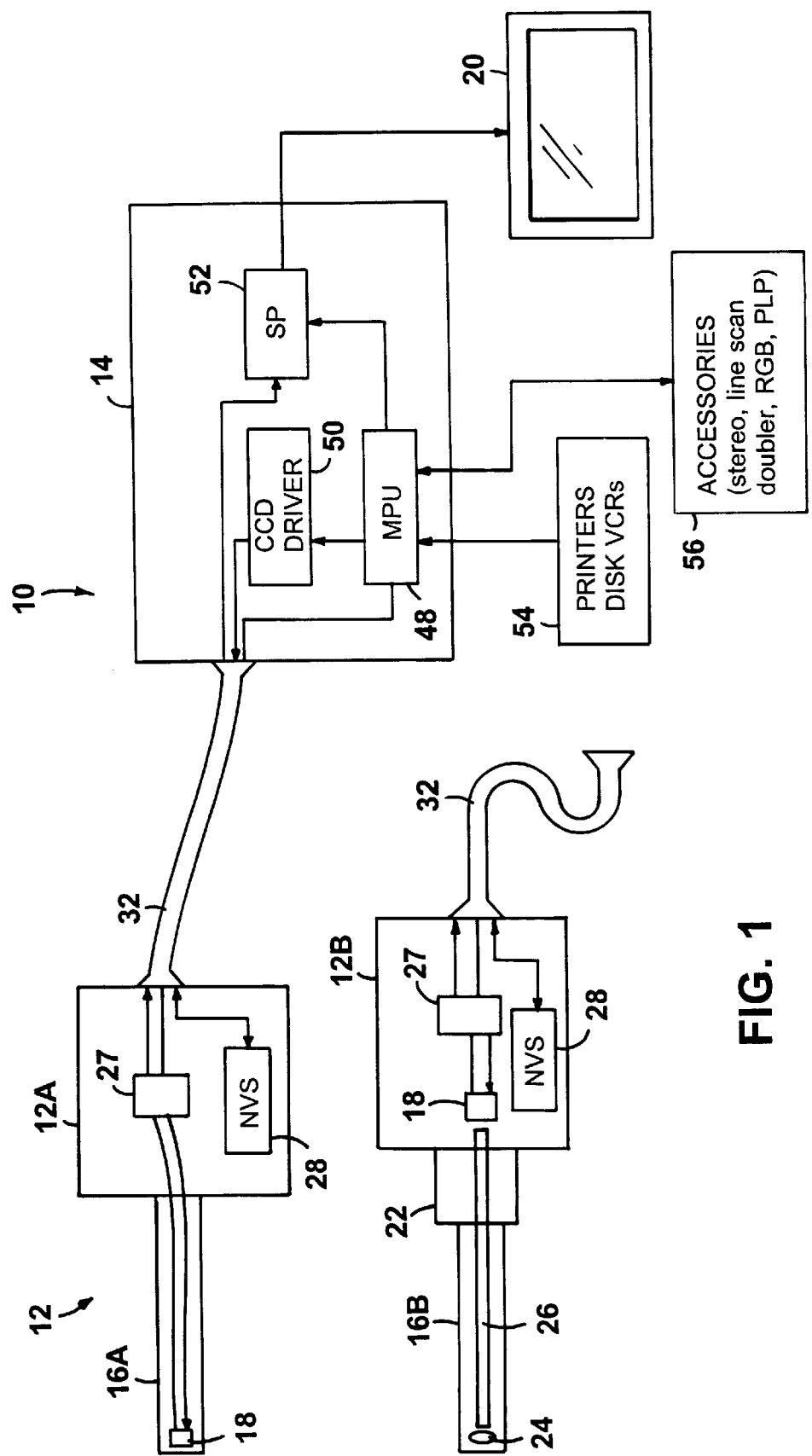
FIGS. 1–2 are block diagrams of a video endoscopy system.

Referring to FIG. 1, a video endoscopy or borescope system 10 includes a camera head 12 and a camera processor 14. Camera head 12 includes an endoscope 16 for insertion into a region such as a body cavity, and an imaging device, such as a CCD 18, that produces electrical signals representative of an optical image at the distal end of endoscope 16. Camera processor 14 processes the electrical signals produced by camera head 12 to generate a video image that is displayed on a video monitor 20.

By varying parameters such as the type of endoscope, the endoscope mount, and the CCD optical format size, camera head 12 can be configured in numerous ways, all of which can produce different electrical signals to represent the same optical image. As illustrated in FIG. 1, camera head 12A includes an electronic endoscope 16A, while camera head 12B includes an optical endoscope 16B. Electronic endoscope 16A is integrally connected to camera head 12A and has a CCD 18 positioned behind focussing optics (not shown) at its distal end. By contrast, optical endoscope 16B has a mount 22 for attachment to camera head 12B, and includes an optical lens 24 positioned at its distal tip and an optical fiber 26 or relay lens assembly that transmits an image from optical lens 24 to a CCD 18 positioned, with support circuitry 27, within camera head 16B.

Mount 22 can have numerous configurations. For example, mount 22 may be a so-called "C-mount," a "V-mount," a direct view scope mount that allows the optical image to be viewed both directly through an eyepiece and at video monitor 20.

Popular optical format sizes for CCD 18 include a one-half inch and a one-third inch size, but other format sizes could also be used. As further illustration of the variety of camera heads 12 that are available, it is noted that Smith & Nephew Dyonics, Inc., Video Division, of Oklahoma City, Okla., markets electronic endoscopes and stereo electronic endoscopes with one-third inch CCDS, as well as V-mount, C-mount, and direct view scope mount optical endoscopes with one-half inch CCDs.

Figure 2:
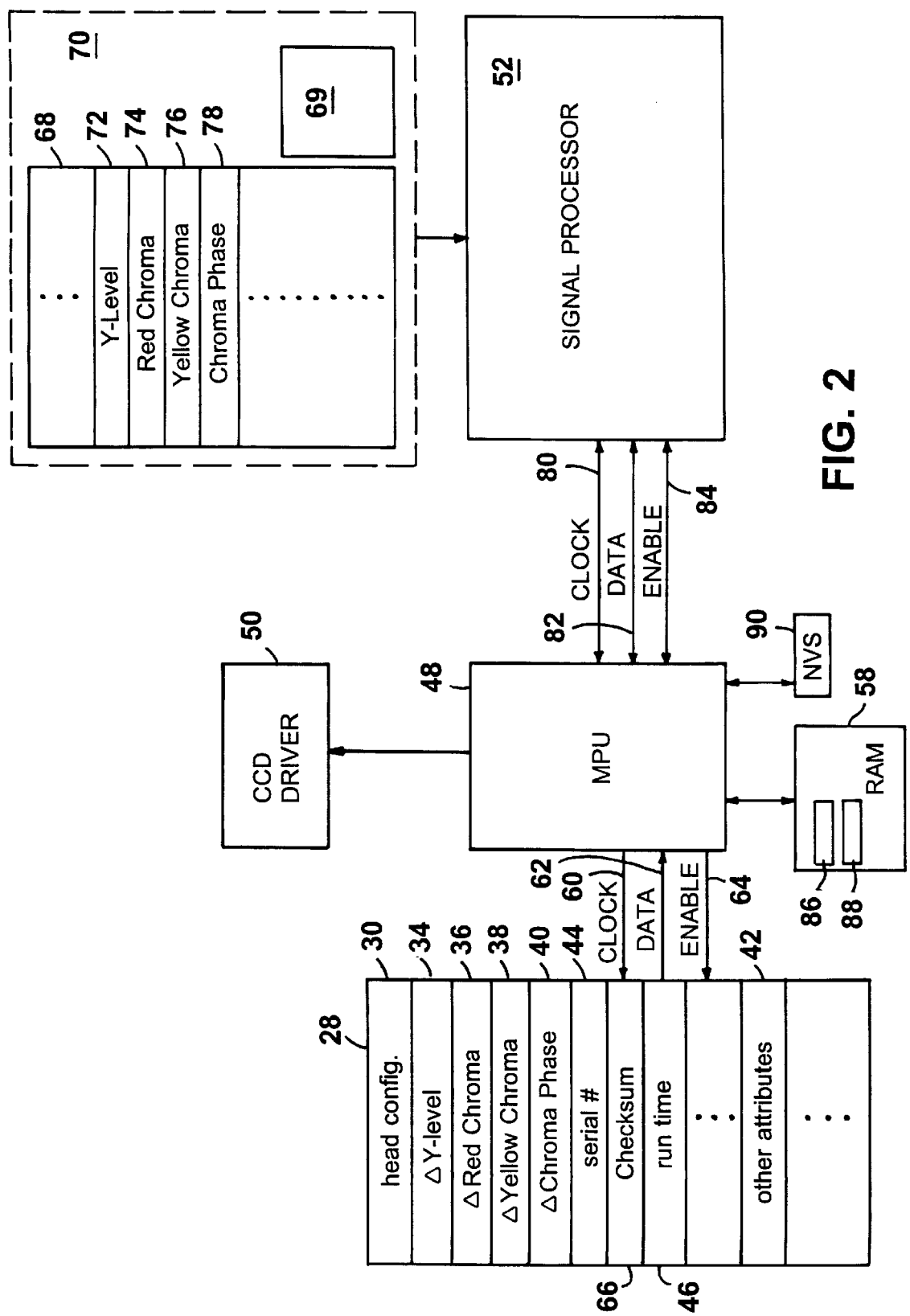

Referring also to FIG. 2, to enable different types of camera heads 12 to be used with camera processor 14 without impacting the quality of the video image displayed on video monitor 20, each camera head 12A, 12B (referred to generally with reference numeral 12) includes a non-volatile storage device ("NVS") 28 that stores information identifying the configuration 30 of the particular camera head 12A, 12B. Camera processor 14 uses the information stored in NVS 28 to modify processing of the electrical signals produced by camera head 12, and thereby accounts for the properties of the configuration 30 to which camera head 12 belongs. In a preferred embodiment, NVS 28 is implemented as an electrically erasable programmable read only memory ("EEPROM"). One such EEPROM is an eight pin, 256 byte storage capacity memory available from the Xicor Corp. as model number 24XC02.

In addition to variations caused by the configuration of camera head 12, the electrical signals produced by camera head 12 can also vary, because performance characteristics of camera heads 12 tend to vary from device to device. These variations, which are caused primarily by differences in optics, CCDs 18, and cables 32 that are attached to camera heads 12 and connect camera heads 12 to camera processor 14, can adversely affect the ability of a camera head 12 to produce electrical signals that result in an optimal video image. Thus, to further ensure consistent performance when different camera heads 12 are used, NVS 28 also stores information that identifies variations in the performance characteristics of a particular camera head 12 from nominal values.

Particular characteristics for which variation data is stored include delta Y-level 34, which represents variations from a nominal value of the magnitude of the signal produced by camera head 12; delta Red-chroma 36, which represents the degree to which red signals produced by camera head 12 diverge from true red; delta Yellow-chroma 38, which represents the degree to which yellow signals produced by camera head 12 diverge from true yellow; and delta chroma phase 40, which affects all colors produced by camera head 12 and is typically caused by variations in a color filter (not shown) of CCD 18.

To enable the video image produced at video monitor 20 to be optimized for certain procedures, the NVS 28 of a camera head 12 designed for those procedures can include information 42 that is used by camera processor 14 to optimize certain signal processing attributes. For example, in a camera head 12 designed for procedures requiring improved edge definition, NVS 28 stores edge enhancement information 42 that replaces nominal edge enhancement values stored within and used by camera processor 14. Similarly, in camera heads 12 designed for procedures in which the white or grey brightness ranges are of particular interest, NVS 28 stores information 42 that modifies, respectively, operation of the so-called "knee circuit" (which implements a nonlinear function for compressing, rather than clipping, the upper level, white, component of the video signal) and the operation of the so-called "gamma circuit" (which implements a nonlinear function for optimizing the median level, grey, component of the video signal) implemented by signal processor 14.

For servicing and other purposes, NVS 28 also stores information that identifies the serial number 44 of camera head 12 and a measure 46, in minutes and hours, of the run time that camera head 12 has experienced.

As shown in FIG. 1, camera processor 14 includes a microprocessing unit ("MPU") 48, a CCD driver 50, and signal processing ("SP") circuitry 52. In operation, MPU 48 provides control to CCD driver 50 for transmitting driving signals to CCD 18 in camera head 12. In response to the driving signals, CCD 18 produces electrical signals representing an image of objects within the field of view of CCD 18, and transmits the electrical signals to signal processing circuitry 52. Signal processing circuitry 52 processes the electrical signals from CCD 18 and converts them to video signals for displaying the image on video monitor 20.

MPU 48 includes ports for connection to auxiliary devices 54, such as printers, disks, and VCRs, and for connection to accessories 56, such as stereo endoscopy systems, line scan doublers, RGB (red, green, blue) generators, and picture-in-picture ("PIP") systems.

Figure 3:
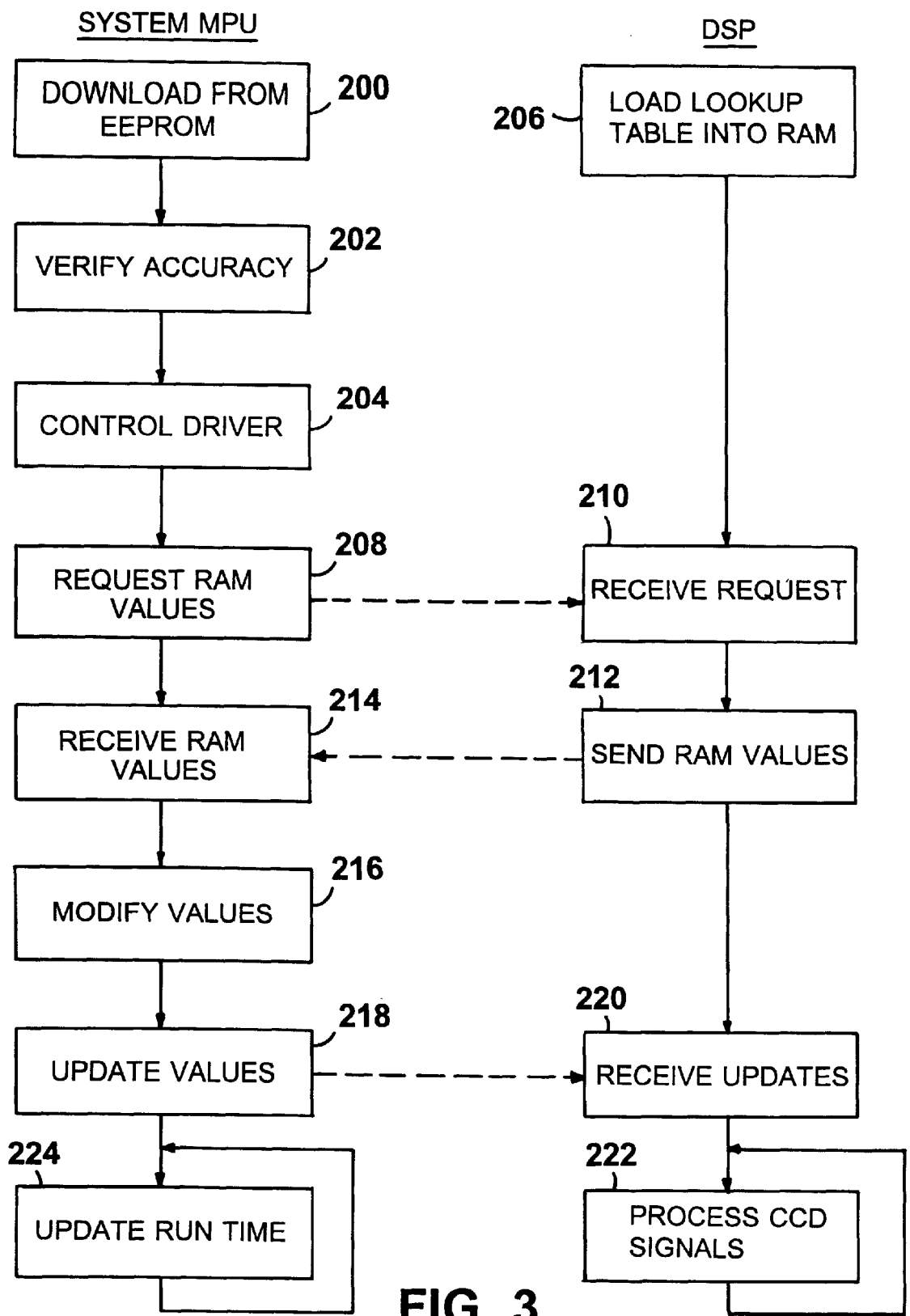
FIG. 3 is a flow chart of a procedure implemented by a processor of the video endoscopy system of FIGS. 1–2.

Referring also to FIG. 3, MPU 48 uses the information stored in NVS 28 to control the operation of CCD driver 50 and signal processing circuitry 52. When the user connects cable 32 of camera head 12 to camera processor 14, and, if necessary, powers up video endoscopy system 10, MPU 48 detects the connection and responds by downloading the information from NVS 28 into a memory 58, such as a RAM, of MPU 48 (step 200). MPU 48 reads the stored information out of NVS 28 through a serial data link in cable 32 that includes a CLOCK line 60 controlled by MPU 48 and a DATA line 62 that is shared by NVS 28 and MPU 48. MPU 48 also controls an ENABLE line 64 that allows NVS 28 to be programmed or erased. To prevent any interference with the electrical signals produced by CCD 18 during active video trace time, MPU 48 reads the information from NVS 28 during the video blanking and vertical retrace times of CCD 18. In particular, this approach avoids capacitive coupling between the CLOCK and DATA lines 60, 62 and the lines that carry electrical signals from CCD 18 within cable 32. This helps avoid interference with the electrical signals produced by CCD 18 and any resulting interference in the video image displayed on video monitor 20.

Next, MPU 48 examines a checksum entry 66 (FIG. 2) from NVS 28 to determine if the information downloaded from NVS 28 is valid, and whether there are electrical problems with the serial data link between MPU 48 and NVS 28 (step 202). Checksum entry 66 is based on other entries of NVS 28. If checksum entry 66 does not verify that the data from NVS 28 is valid, then NPU 48 does not proceed any further, and signal processing circuitry 52 processes the electrical signals from CCD 18 without consideration of the information stored in the entries of NVS 28.

After verifying the accuracy of the information obtained from NVS 28, MPU 48 uses the information contained to control CCD driver 50 (step 204). For example, the phase of the drive signals produced by CCD driver 50 when the size of CCD 18 is a one-half inch differ from the phase when the size is a one-third inch. MPU 48 modifies the phase of the driver signals based on the size of CCD 18 as reflected in configuration entry 30 of NVS 28.

While MPU 48 is downloading values from NVS 28 and verifying their accuracy, signal processing circuitry 52 loads signal processing information from a lookup table 68 stored in a memory 70, such as a RAM, associated with signal processing circuitry 52 into other storage locations 69 in memory 70 (step 206). In addition to other signal processing parameters, lookup table 68 includes entries for Y-level 72, red chroma 74, yellow chroma 76, and chroma phase 78. Information contained in entries 72–78 is copied into storage locations 69.

Entries 72–78 of lookup table 68 represent nominal values for their respective parameters, and entries 34–40 of NVS 28, respectively, represent variations from these nominal values. To account for the variations, MPU 48 first requests the values of the entries from memory 70 that correspond to entries 62–68 of lookup table 68 (step 208). Upon receiving this request (step 210), signal processing circuitry 52 sends the values to MPU 48 (step 212).

MPU 48 communicates with signal processing circuitry 52 through a bidirectional serial data link that includes a CLOCK line 80 controlled by MPU 48 and a DATA line 82 that is shared by MPU 48 and signal processing circuitry 52. MPU 48 also controls an ENABLE line 84 that activates external control of signal processing circuitry 52.

When MPU 48 receives the values corresponding to table entries 72–78 from signal processing circuitry 52 (step 214), MPU 48 modifies the values based on the corresponding values from entries 34–40 of NVS 28 (step 216). For example, when MPU 48 receives the value corresponding to Y-level 72 from lookup table 68, MPU 48 modifies the value by adding or subtracting the value corresponding to delta Y-level entry 34 from NVS 28. Alternatively, rather than using a linear operation such as addition or subtraction, MPU 48 can modify the values using curve fitting or other non-linear (e.g., logarithmic) techniques.

After modifying the values of table entries 72–78 received from signal processing circuitry 52, MPU 48 transmits the updated values to signal processing circuitry 52 (step 218). When entries from NVS 28 reflect replacement values for entries in lookup table 68, MPU 48 transmits the replacement values (step 218) without requesting values from signal processing circuitry and modifying those values (steps 208–216).

After signal processing circuitry 52 receives the updated values from MPU 48 (step 220), signal processing circuitry 52 uses the updated values in processing the electrical signals from CCD 18 for display on video monitor 20 (step 222). That is, signal processing circuitry 52 uses the updated values in locations 69—rather than the nominal values from lookup table 68—in performing the conversion of the electrical signals from CCD 18 to video signals.

After updating the entries in memory 70 of signal processing circuitry 52, MPU 48 uses the bidirectional serial data link (60–64) connecting MPU 48 and NVS 28 to periodically update run time value 76 stored in NVS 28 (step 224). MPU 48 uses internal timers (not shown) to measure the run times of camera head 12 and camera processor 14 and update corresponding entries 86, 88 in RAM 58. Periodically (such as once every four minutes), MPU 48 writes the camera head run time information from entry 86 into run time entry 46 of NVS 28 (FIG. 2). More frequently (such as once per minute) MPU 48 uses timer entry 88 to update a run time value for camera processor 14 stored in non-volatile storage 90 connected to MPU 48.

Referring to FIG. 4, in a more detailed view, camera head 12 includes CCD 18 (located, as discussed, either in the head or at the tip of the endoscope), NVS 28 and a set of button switches 92 for system control, and camera processor 14 includes a camera controller 94 and a signal processor 96. Cable 32, which connects camera head 12 to camera processor 14, carries drive signals from CCD driver 50 in signal processor 96, electrical signals from CCD 18 to a preamplifier 98 in signal processor 96, data between NVS 28 and MPU 48 in camera controller 94, and signals from button switches 92 to MPU 48.

MPU 48 controls signal processor 96 in response to signals from button switches 92 and signals from controls in a front panel 100 of camera controller 94. The controls in front panel 100 allow the user of video endoscopy system 10 to configure button switches 92 to perform desired functions. Thus, for example, button switches 92 could be configured to cause signal processor 96 to pause the video image displayed at video monitor 20 (FIG. 1). MPU 48 also displays system parameters at front panel 100, interacts with NVS 28 by downloading information about camera head 12 and updating run time information in NVS 28, updates signal processing parameters in light of the information about camera head 12, and communicates with signal processor 96, all as discussed above.

Signal processor 96 is implemented using a camera that is available from Panasonic as model number KS152. (Alternatively, signal processor 96 may be implemented using another digital camera, an analog camera with a digital interface, or custom circuitry.) Signal processor 96 includes a signal processing controller 102 that controls the procedure by which signal processor 96 produces a video image for display. Initially, signal processing controller 102 controls CCD driver 50 to produce drive signals that drive CCD 18. (As discussed above, the output of CCD driver 50 is modified based on the configuration of camera head 12 as set forth in entry 30 of NVS 28 (FIG. 2).)

When CCD 18 produces electrical signals in response to the drive signal from CCD driver 50, cable 32 carries the electrical signals to preamplifier 98, which is controlled by signal processing controller 102 to ensure that an output of preamplifier 98 has a proper voltage level. Signal processing controller 102 also modifies the gain of preamplifier 98 based on the configuration of camera head 12 as set forth in entry 30 of NVS 28. For example, a one-half inch CCD 18 produces different voltage levels than a one-third inch CCD 18, and the gain of preamplifier 98 is adjusted accordingly.

The output of preamplifier 98 is connected to the input of a sample and hold circuit 104 that passes only portions of the output. The output of sample and hold circuit 104 is supplied to an analog processing circuit 106 that is also controlled by signal processing controller 102. In controlling analog processing circuit 106, signal processing controller 102 uses values from lookup table 68 that have been loaded into memory 70. As discussed above, if these values have been modified or replaced by MPU 48 based on information from NVS 28 of camera head 12, then analog processing circuit 106 will be affected by the new values.

An analog to digital converter 108 converts the output of analog processing circuit 106 into a digital signal, and supplies the digital signal to a digital signal processor (DSP) 110 that is controlled by signal processing controller 102. Once again, signal processing controller 102 controls digital signal processor using values from memory 70 that can be modified or replaced by MPU 48 in response to information from NVS 28 of camera head 12.

The output of digital signal processor 110 passes through a digital to analog converter 112 and is encoded according to standard Y/C and composite video protocols by an encoder 114.

As discussed, in controlling the various components of signal processor 96, signal processing controller 102 relies on entries from lookup table 68 that are stored in locations 69 of memory 70. Because, as discussed above, the entries in memory 70 are modified by MPU 48 in light of entries from NVS 28, the processing performed by the various components of signal processor 96 reflects the configuration of camera head 12, as well as variations in performance characteristics of camera head 12.

Other embodiments are within the scope of the following claims.

For example, although an endoscope for visually inspecting a body cavity has been described, the invention is equally applicable for use with borescopes or other visualization devices.

NVS 28 may store information about camera head configurations and performance characteristics other than, or in addition to, those discussed above.

Moreover, through use of non-volatile storage that can withstand autoclave temperatures without adverse effect, a camera head 12 that is autoclavable can be produced. Xicor manufactures EEPROMs suitable for use as non-volatile storage devices in autoclavable instruments.

What is claimed is:

1. Apparatus for providing electrical signals that represent an optical image to a processor for conversion to video signals that represent said optical image and which are suitable for display on a display device, said apparatus comprising, a device operable to be inserted into a region to be viewed for developing an optical image of said region, an imager supported by said device and operable to generate electrical signals that represent said optical image, a digital memory supported by said device and storing information about said imager for use by the processor in converting the electrical signals produced by said imager to said video signals that represent said optical image, said information including information identifying variations in performance characteristics of said imager relative to nominal performance characteristics, and said device being adapted for connection to the processor so that the processor can receive said electrical signals from said imager and obtain said information from said digital memory for use in converting the electrical signals from said imager to said video signals that represent said optical image, wherein said received electrical signals are distinct from said information from said digital memory.

2. The apparatus of claim 1 wherein said information stored in said digital memory includes information identifying a configuration of said imager.

3. The apparatus of claim 2 wherein said information identifying said configuration of said imager includes information identifying a location of said imager relative to said device.

4. The apparatus of claim 3 wherein said information identifying said location of said imager relative to said device indicates that said imager is located at a distal end of said device.

5. The apparatus of claim 4 wherein said information identifying said location of said imager relative to said device indicates that said imager is located at a proximal end of said device.

6. The apparatus of claim 2 wherein said imager includes a charge coupled device and said information identifying a configuration of said imager identifies an optical format size of said charge coupled device.

7. The apparatus of claim 1, further comprising a processor and storage for values of said nominal performance characteristics, said processor being operable to receive said electrical signals from said imager, to obtain said information from said digital memory, and to convert said electrical signals to video signals that represent said optical image and are suitable for display using said information and said values of said nominal performance characteristics.

8. The apparatus of claim 1 wherein said device comprises an endoscope.

9. The apparatus of claim 1 further comprising optics for producing said optical image, wherein said information identifying variations in performance characteristics of said imager accounts for variations in performance characteristics of said optics relative to nominal performance characteristics.

10. The apparatus of claim 1 wherein said imager includes a charge coupled device and said information identifying variations in performance characteristics of said imager accounts for variations in performance characteristics of said charge coupled device relative to nominal performance characteristics.

11. The apparatus of claim 1 further comprising a cable for connection to said processor, wherein said information identifying variations in performance characteristics of said imager accounts for variations in performance characteristics of said cable relative to nominal performance characteristics.

12. The apparatus of claim 1 wherein said information identifying variations in performance characteristics of said imager relative to nominal performance characteristics identifies variations in luminance reproduction of said imager.

13. The apparatus of claim 1 wherein said information identifying variations in performance characteristics of said imager relative to nominal performance characteristics identifies variations in color reproduction of said imager.

14. The apparatus of claim 1 wherein said information stored in said digital memory includes information identifying characteristics of said region to be viewed by said imager.

15. The apparatus of claim 1 wherein said device is adapted for connection to said processor so that said processor can update information stored in said digital memory.

16. The apparatus of claim 15 wherein said information stored in said digital memory includes run time information that measures wear on said imager, and wherein said device is adapted so that said processor updates the run time information.

17. The apparatus of claim 1 wherein the digital memory is a non-volatile storage device.

18. The apparatus of claim 17 wherein the non-volatile storage device is an EEPROM.

19. Apparatus for representing an optical image as video signals suitable for display on a display device, said apparatus comprising:
   a device operable to produce electrical signals representative of an optical image of a region to be viewed, said device including:
      a portion operable to be inserted into said region to be viewed for developing an optical image of said region,
      an imager operable to generate electrical signals that represent said optical image, and
      a digital memory storing information about said device; and
   a processor connected by a cable to said device, said processor being operable to receive said electrical signals from said imager over said cable, to access said digital memory and read said information from said digital memory over said cable, and to convert said electrical signals using said information to video signals that represent said optical image and are suitable for display, wherein said received electrical signals are distinct from said information from said digital memory.

20. The apparatus of claim 19 wherein said information stored in said digital memory includes information identifying a configuration of said device, and wherein said processor modifies said conversion based on said configuration.

21. The apparatus of claim 19 wherein said processor stores information identifying nominal values of performance characteristics for said device, said digital memory includes information identifying variations in performance characteristics of said device relative to said nominal values of performance characteristics, and said processor modifies said conversion based on said variations in performance characteristics.

22. The apparatus of claim 19 wherein said processor updates information stored in said digital memory.

23. The apparatus of claim 22 wherein said information stored in said digital memory includes run time information of said device, said processor updating the run time information.

24. The apparatus of claim 22, wherein said processor converts said electrical signals into said video signals during a first time period and not during a second time period, said processor updating the information stored in the digital memory only during said second time period.

25. The apparatus of claim 19 further comprising a driver that produces driving signals for said imager, wherein said information stored in said digital memory includes information identifying a configuration of said device, and wherein said processor signals said driver to modify said driving signals based on the information identifying the configuration of said device.

26. The apparatus of claim 19 wherein said information stored in said digital memory includes verification information that verifies whether said information stored in said digital memory is valid, and wherein said processor uses said verification information to determine whether said information stored in said digital memory is valid and whether said processor has received said information correctly.

27. The apparatus of claim 19 further comprising a memory having entries in which are stored signal processing parameters used by said processor in performing said conversion, and wherein said processor modifies said conversion by modifying entries of said memory that relate to information received from said digital memory of said device.

28. The apparatus of claim 1, wherein said apparatus is configured to be autoclavable without damage to the apparatus.

29. The apparatus of claim 19, wherein said device is configured to be autoclavable without damage to the device.

30. Apparatus for providing electrical signals that represent an optical image to a processor for conversion to video signals suitable for display on a display device, said apparatus comprising:
   a device operable to be inserted into a region to be viewed for developing an optical image of said region,
   an imager supported by said device and operable to generate electrical signals that represent said optical image,
   a digital memory supported by said device and storing information identifying variations in luminance reproduction of said imager relative to nominal luminance reproduction for use by the processor in converting the electrical signals produced by said imager to video signals, and
   said device being adapted for connection to the processor so that the processor can receive said electrical signals from said imager and obtain said information from said digital memory for use in converting the electrical signals from said imager to video signals, wherein said electrical signals from said imager are distinct from said information from said digital memory.

31. The apparatus of claim 30, wherein the information stored in said memory is suitable to permit the processor to correct for luminance reproduction variations in the imager-produced electrical signals.

32. Apparatus for providing electrical signals that represent an optical image to a processor for conversion to video signals suitable for display on a display device, said apparatus comprising, a device operable to be inserted into a region to be viewed for developing an optical image of said region, an imager supported by said device and operable to generate electrical signals that represent said optical image, a digital memory supported by said device and storing information identifying variations in color reproduction of said imager relative to nominal color reproduction for use by the processor in converting the electrical signals produced by said imager to video signals, and said device being adapted for connection to the processor so that the processor can receive said electrical signals from said imager and obtain said information from said digital memory for use in converting the electrical signals from said imager to video signals, wherein said electrical signals from said imager are distinct from said information from said digital memory.

33. The apparatus of claim 32, wherein the information stored in said memory is suitable to permit the processor to correct for color reproduction variations in the imager-produced electrical signals.

34. An endoscope for providing electrical signals that represent an optical image of an object, comprising, a housing, at least a portion of which is configured to be inserted into a region to be viewed for developing an optical image of said region, an imager mounted in said housing and operable to generate electrical signals that represent said optical image, a digital memory mounted in said housing and storing information identifying variations in said electrical signals relative to nominal values of said electrical signals, and circuitry operable to provide said electrical signals and said information to an output of said endoscope, wherein said electrical signals from said imager are distinct from said information from said digital memory.

35. The endoscope of claim 34 wherein said information stored in said digital memory includes information identifying a configuration of said imager.

36. The endoscope of claim 35 wherein said information identifying said configuration of said imager includes information identifying a location of said imager within said housing.

37. The endoscope of claim 35 wherein said imager includes a charge coupled device and said information identifying a configuration of said imager identifies an optical format size of said charge coupled device.

38. The endoscope of claim 34 further comprising optics for producing said optical image, wherein said information stored in said memory accounts for variations in performance characteristics of said optics relative to nominal performance characteristics.

39. The endoscope of claim 34 wherein said information stored in said memory identifies variations in luminance reproduction of said imager.

40. The endoscope of claim 34 wherein said information stored in said memory identifies variations in color reproduction of said imager.

* * * * *